United States Patent [19]

Alexander, III

[11] 4,387,590
[45] Jun. 14, 1983

[54] SWATCH REMOVER AND METHOD

[76] Inventor: William J. Alexander, III, 41 W. Golden Strip Dr., Mauldin, S.C. 29662

[21] Appl. No.: 269,678

[22] Filed: Jun. 2, 1981

[51] Int. Cl.³ ............................................. G01N 1/04
[52] U.S. Cl. ........................................ 73/159; 26/70; 73/864.41; 83/83
[58] Field of Search ...................... 83/83; 73/863, 864, 73/864.41; 26/70

[56] References Cited

U.S. PATENT DOCUMENTS

| | | | |
|---|---|---|---|
| 2,834,558 | 5/1958 | Halpern | 26/70 |
| 3,276,303 | 10/1966 | Tompos | 73/864.41 |
| 3,322,363 | 5/1967 | Davidson et al. | 226/11 |
| 3,906,824 | 9/1975 | Morgan | 83/83 |
| 3,939,034 | 2/1976 | Tanaka et al. | 242/58.5 |
| 4,082,589 | 4/1978 | Patterson | 226/28 |

*Primary Examiner*—S. Clement Swisher
*Attorney, Agent, or Firm*—Ralph Bailey

[57] ABSTRACT

A swatch remover for sampling a web such as fabric or cloth moving in open width from a loom to take-up mechanism is illustrated as having an upright transverse frame member which is pivoted outboard of the winder adjacent each end thereof, and which may be pivoted downwardly for facilitating the extending of a length of cloth for swatch removal and later rejoining as by sewing.

4 Claims, 3 Drawing Figures

SWATCH REMOVER AND METHOD

BACKGROUND OF THE INVENTION

The use of various sewing apparatus such as railway sewing machines are common expedients for joining or splicing lengths of cloth in open width such as for facilitating the attachment of lengths of cloth during finishing, or where swatches and the like are cut from the cloth. U.S. Pat. Nos. 3,322,363; 3,939,034 and 4,082,589 appear to be representative of the prior art. The prior art devices used for swatch removal require more than one person pulling on either side of the cloth for extending the length to facilitate swatch removal. The cloth is then positioned manually for the rejoining of the ends as through a sewing operation.

Accordingly, it is an important object of the present invention to facilitate the removal of swatches from a length of cloth as during winding or finishing which may be accomplished by a single operator wherein a vertical frame having a bar over which the cloth passes may be pivoted downwardly with the bar extended for lengthening the cloth which has been released from the winder side of the assembly.

SUMMARY OF THE INVENTION

It has been found that removal of swatches for sampling may be facilitated by utilizing a vertical frame having a bar at the top over which the cloth passes to the winder mechanism. The frame is pivoted adjacent the bottom outboard of the winder so as to be pivoted downwardly by an operator and then further extended through removing the bar from the frame and pulling same outwardly, arranging the cloth for cutting and reception for sewing on the standard type of railway sewing apparatus. The method contemplates that the cloth be released from the winder to permit the formation of the cloth loop for removal as a swatch.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

A swatch removing apparatus is provided for use with a cloth winder and the like. An upright transverse frame member A is pivoted outboard of the winder adjacent each end thereof having a bridging member adjacent the top over which cloth passes in open width to the winder. Means B limits downward pivoted movement of the transverse frame member for receiving cloth, a length of which has been pulled outwardly of a path to the winder by movement of the bridging member as a result of downward pivotal movement of the frame for removal as a swatch. Means C positions the cloth for joining the ends of cloth resulting from removal of the swatch together after removal of the swatch. A bar D is removably carried by the bridging members outwardly thereof for extending the length of cloth to facilitate swatch removal. A central handle E is pivotally connected at each end to a respective end of the bar so that the bar may be removed and the length of cloth extended by one person. The method also contemplates simultaneously permitting a release of the cloth by the winder for said pulling of a length of cloth, and then withdrawing a further length of cloth for swatch removal by moving the bar outwardly.

Figure 1:
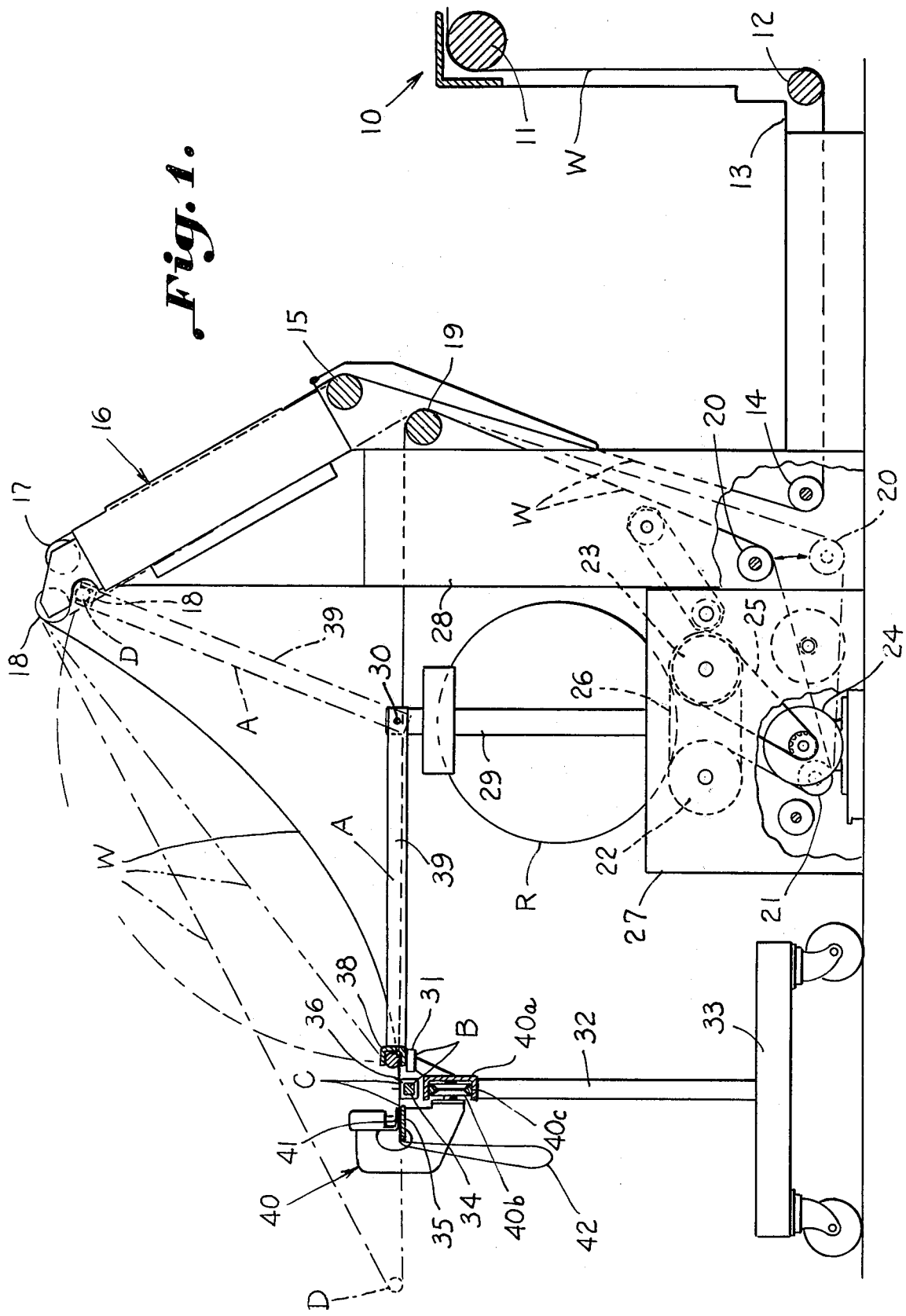
FIG. 1 is a schematic side elevation illustrating a loom winder equipped with a swatch remover constructed in accordance with the present invention, illustrating the method of the invention.

Referring more particularly to the drawings, a loom is broadly designated at 10 in FIG. 1 and the cloth or web W is illustrated as passing downwardly over the roll 11 and beneath a guide roll 12 prior to passing beneath an operator's platform 13. The web passes from beneath the operator's platform and over a guide roll 14 prior to passing over a guide roll 15 which carries the cloth over an inspection apparatus broadly designated at 16. The cloth then passes the guide rolls 17 and 18 and thence over a bar D on its passage downwardly to a guide roll 19 and thence to an oscillating guide roll or dancer 20 prior to its passage over a guide roll 21 from whence it is guided to the support rolls 22 and 23 of a surface winder arrangement.

The support rolls are illustrated as being driven by a motor 24 through a drive chain 25. A chain 26 drives the roll 22 from a sprocket carried in fixed relation to the roll 23. The driving components are carried within a suitable frame member 27 and various guide members are carried within the standard 28 which positions the inspection apparatus. A pair of upright frame members 29 are carried on both sides outside the frame member 27 to which they are suitably secured adjacent their lower portions. The upright transverse frame member A is pivotally connected as at 30 on its lower end outboard of the winder. Means B may be provided in the form of a stop member 31 which has attachment to the vertical frame member 32 of a wheeled dolly 33. The dolly 33 has means for fixing the wheels against rotation (not shown), for securing the dolly in a desired position in relation to the winder. The stop means B may simply consist of a bar 34 which will act as a desirable limit to downward movement of the frame member A when the fabric is in extended position to form a swatch.

The means C for positioning the cloth for joining the ends of the cloth after removing the swatch include a sewing machine broadly designated at 40 and a slidable bracket 36 which carries a pin 37 (FIG. 2) for securing the outer edges of the fabric by the operator after the bar D, which is carried atop the transverse frame A is extended to dotted line position, as shown in FIG. 1. The bar D is carried within a channel member 38 suitably secured as by welding to the vertical frame members which form the pivoted downwardly extending members of the upright transverse frame member A.

Figure 2:
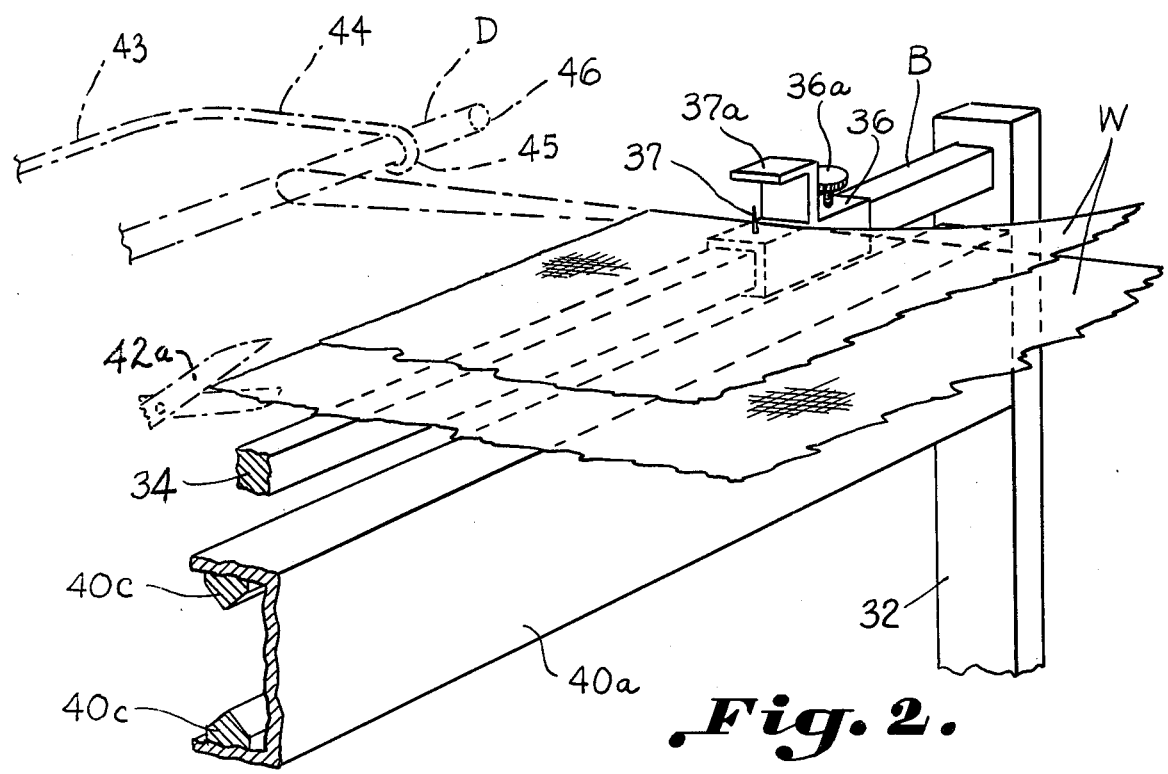
FIG. 2 is a perspective view looking from the rear of the swatch removing apparatus illustrated in FIG. 1.
Figure 3:
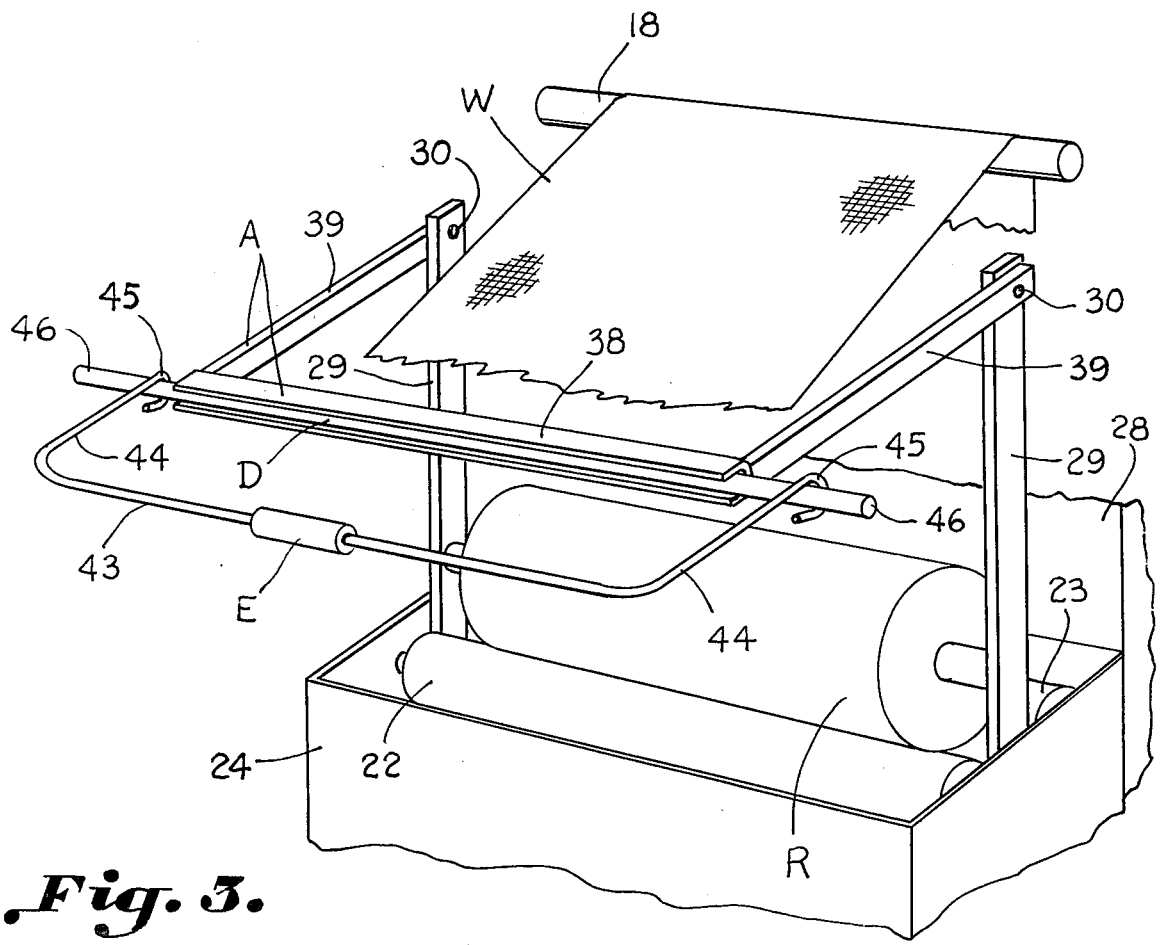
FIG. 3 is a perspective view taken from the front of the swatch forming apparatus of FIG. 1.

The railway sewing machine, illustrated broadly at 40, includes a presser foot 41 positioned opposite the sewing machine plate 35 between which the cloth passes as illustrated in FIG. 1 hanging downwardly in the form of a loop 42. The cloth 42 is then severed away as by an automatic cutter, or simply by shears 42a (FIG. 2).

In forming the depending loop 42, the bar D is extended after pivoting the frame A downwardly. This is accomplished by releasing the cloth from the winder so that it may be extended rearwardly as illustrated in FIG. 1. The handle E of a removable gripping apparatus includes an intermediate portion 43 and legs extending outwardly therefrom at 44 together with a loop at each end 45 for temporary or permanent attachment to a shaft portion 46 extending outwardly from each end of the bar D. By using the aforesaid method, it is possible for a single operator to remove the necessary swatch for use in the lab to examine the quality and dyeability of the cloth.

The cloth or web W is illustrated as being released from the surface wound roll R by the winder mechanism and then being moved outwardly to form loop 42 when the bar D is pulled outwardly by the centrally disposed handle E. The sewing machine is illustrated as being carried upon a transverse rail 40a positioned atop the vertical frame members 32a carried by the dolly 33. The wheels 40b which support the sewing machine on the rails for horizontal transport transversely of the cloth are carried on the rails 40c positioned on respective flanges of the outwardly facing channel member 40a.

The outer edges of the cloth which is tensioned slightly through widthwise stretch are fastened onto pins 37 which are carried on the slidable bracket 36 on the rail 34. The bracket is positioned to maintain the widthwise stretch as through the tightening of the threadable member 36a. An overlying protector shield is illustrated at 37a which extends over the pin 37 to prevent accidental injury. Thus, a single operator may pivot the frame A downwardly and pull outwardly on the bar D through the centrally disposed handle E to form a loop from the cloth which has been let-off from the cloth roll R. The shears 42a may then be used to trim off the swatch from a position well in advance of the needle of the sewing machine to provide for an even rejoining of the cloth through operation of the sewing machine on the cloth which is held evenly in widthwise stretch position upon the pins 37a on either side thereof.

Thus, the removal of a swatch which has formerly been an awkward operation for several operators is greatly facilitated so that a single operator may now accomplish this properly on a cloth winder as from a loom or other apparatus wherein cloth is moved in open width to be finally gathered into a roll.

While a preferred embodiment of the invention has been described using specific terms, such description is for illustrative purposes only, and it is to be understood that changes and variations may be made without departing from the spirit or scope of the following claims.

What is claimed is:

1. For use with a cloth winder and the like, a swatch removing apparatus comprising:
    an upright transverse frame member pivoted outboard of said winder adjacent each end thereof having a bridging member adjacent the top over which cloth passes in open width to said winder;
    means limiting downward pivoted movement of said transverse frame member for receiving cloth, a length of which has been pulled outwardly of a path to said winder by movement of said bridging member as a result of downward pivotal movement of said frame for removal as a swatch; and
    means for positioning said cloth for joining ends of cloth resulting from removal of the swatch together after removal of the swatch.

2. The structure set forth in claim 1 including a bar removably carried by said bridging member outwardly thereof for extending said length of cloth to facilitate swatch removal.

3. The structure set forth in claim 2 including a central handle pivotally connected at each end to a respective end of said bar so that said bar may be removed by one person.

4. The method of removing swatches from an open width of cloth prior to being received by a winder comprising the steps of:
    passing said cloth to the winder in a path extending over a transverse bar which may be moved downwardly and outwardly;
    carrying the cloth therewith outwardly with respect to the winder;
    simultaneously permitting release of said cloth by said winder for said pulling of a length of cloth; and
    withdrawing a further length of cloth for swatch removal by moving said bar outwardly.

* * * * *